US00PP16975P2

(12) United States Plant Patent
Pattison

(10) Patent No.: US PP16,975 P2
(45) Date of Patent: Aug. 8, 2006

(54) ***PLECTRANTHUS* PLANT NAMED 'LIMPLEP 1'**

(50) Latin Name: *Plectranthus parviflorus*
Varietal Denomination: Limplep 1

(75) Inventor: Rod Pattison, Rochedale (AU)

(73) Assignee: Limpinwood Gardens, Limpinwood (AU)

( * ) Notice: Subject to any disclaimer, the term of this patent is extended or adjusted under 35 U.S.C. 154(b) by 0 days.

(21) Appl. No.: 11/000,447

(22) Filed: Nov. 30, 2004

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—C. A. Whealy

(57) ABSTRACT

A distinct cultivar of *Plectranthus* plant named 'Limplep 1', characterized by its upright, mounded and compact plant habit; vigorous and freely branching growth habit; green and creamy white variegated foliage; numerous violet blue-colored flowers on erect flowering spikes; and good garden performance.

1 Drawing Sheet

Botanical classification/cultivar designation: *Plectranthus parviflorus* cultivar Limplep 1.

BACKGROUND OF THE INVENTION

The present Invention relates to a new and distinct cultivar of *Plectranthus* plant, botanically known as *Plectranthus parviflorus*, and hereinafter referred to by the name 'Limplep 1'.

The new *Plectranthus* is a naturally-occurring whole plant mutation of an unnamed selection of *Plectranthus parviflorus,* not patented. The new *Plectranthus* was discovered and selected by the Inventor as a single plant from within a population of plants of the parent selection in a controlled environment in Rochedale, Queensland, Australia in 2000.

Asexual reproduction of the new cultivar by cuttings taken in a controlled environment in Brisbane, Queensland, Australia since 2001, has shown that the unique features of this new *Plectranthus* are stable and reproduced true to type in successive generations.

SUMMARY OF THE INVENTION

Plants of the cultivar Limplep 1 have not been observed under all possible environmental conditions. The phenotype may vary somewhat with variations in environment and culture such as temperature and light intensity without, however, any variance in genotype.

The following traits have been repeatedly observed and are determined to be the unique characteristics of 'Limplep 1'. These characteristics in combination distinguish 'Limplep 1' as a new and distinct cultivar of *Plectranthus:*

1. Upright, mounded and compact plant habit.
2. Vigorous and freely branching growth habit.
3. Green and creamy white variegated foliage.
4. Numerous violet blue-colored flowers on erect flowering spikes.
5. Good garden performance.

Plants of the new *Plectranthus* are most similar to plants of the parent selection. In side-by-side comparisons conducted in Brisbane, Queensland, Australia, plants of the new *Plectranthus* differed from plants of the parent selection in the following characteristics:

1. Plants of the new *Plectranthus* had variegated foliage whereas plants of the parent selection had nonvariegated foliage.
2. Plants of the new *Plectranthus* had darker violet blue-colored flowers than plants of the parent selection.

Plants of the new *Plectranthus* can also be compared to plants of the *Plectranthus* cultivar P000603, disclosed in U.S. Plant Pat. No. 16,002. Plants of the new *Plectranthus* differ primarily from plants of the cultivar P000603 in leaf and flower coloration as plants of the cultivar P000603 have dark green-colored leaves and pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Plectranthus.*

The photograph at the bottom of the sheet comprises a side perspective view of a typical flowering plant of 'Limplep 1'.

The photograph at the top of the sheet comprises a close-up view of a typical leaves and flowers of 'Limplep 1'.

DETAILED BOTANICAL DESCRIPTION

The aforementioned photographs and following observations and measurements describe plants grown in Bonsall, Calif., under commercial practice during the summer in an outdoor nursery with day temperatures ranging from 18 to 35° C. and night temperatures ranging from 10 to 21° C. Plants were grown with one rooted cutting per 10-cm container for about seven weeks. In the following description, color references are made to The Royal Horticultural Society Colour Chart, 1995 Edition, except where general terms of ordinary dictionary significance are used.

Botanical classification: *Plectranthus parviflorus* cultivar Limplep 1.

Parentage: Naturally-occurring whole plant mutation of an unnamed selection of *Plectranthus parviflorus,* not patented.

Propagation:

*Type cutting.*—Vegetative cuttings.

*Time to initiate roots.*—About two weeks at 21° C.

*Time to develop roots.*—About three weeks at 21° C.

*Root description.*—Fine; whitish in color.

*Rooting habit.*—Freely branching; dense.

Plant description:

*Form.*—Upright, mounded and compact plant habit. Freely branching with about five to six primary lateral branches and numerous secondary branches; dense and bushy appearance. Vigorous growth habit.

*Plant height* (*soil level to top of foliage*).—About 25 cm.

*Plant height* (*soil level to top of inflorescences*).—About 41 cm.

*Plant diameter.*—About 33 cm.

*Lateral branches.*—Length: About 23 cm. Diameter: About 5.5 mm. Internode length: About 3 cm. Strength: Moderately strong. Texture: Tomentose. Color: 148A tinged with 60B.

*Foliage description.*—Arrangement: Opposite, simple. Length: About 6 cm. Width: About 4.2 cm. Shape: Elliptic. Apex: Broadly acute; slightly recurved. Base: Attenuate. Margin: Crenate. Aspect: Mostly flat. Texture, upper and lower surfaces: Tomentose; velvety. Venation pattern: Pinnate, arcuate. Petiole length: About 2.5 mm. Petiole diameter: About 2 mm. Petiole texture, upper and lower surfaces: Tomentose; velvety. Color: Developing foliage, upper surface: Center, 146B; towards the margins, 11C. Developing foliage, lower surface: Center, 148C; towards the margins, 11C to 11D. Fully expanded foliage, upper surface: Center, more gray than 137A; towards the margins, 158A. Fully expanded foliage, lower surface: Center, more gray than 147B; towards the margins, 158A to 158B. Venation, upper surface: 148A. Venation, lower surface: More gray than 147B. Petiole, upper and lower surfaces: 148A.

Flower description:

*Flower type and habit.*—Numerous single bilabiate flowers arranged in verticillasters arranged in terminal and axillary spikes. Individual flowers face mostly outward. Freely flowering with about 105 to 120 flowers buds, developing flowers and open flowers per spike. Flowers not persistent.

*Natural flowering season.*—Plants flower from August to November in Southern California; flowering continuous during this period.

*Flower longevity on the plant.*—About four to five days.

*Fragrance.*—None detected.

*Inflorescence length.*—About 15 cm.

*Inflorescence width.*—About 3 cm.

*Flowers.*—Appearance: Zygomorphic; bilabiate. Length: About 1.4 cm. Diameter: About 6 mm.

*Flower buds.*—Length: About 5 mm. Diameter: About 2.5 mm. Shape: Elongated oblong. Color: 156D.

*Corolla.*—Petal arrangement/appearance: Bilabiate; five petals, upper two banner petals fused and lateral and lip petals fused, all five petals fused at base into a tubular structure. Petal length: Banner petals: About 3 mm. Lateral petals: About 1 mm. Lip petal: About 7 mm. Petal width: Banner petals: About 3 mm. Lateral petals: About 1 mm. Lip petal: About 5 mm. Petal shape: Rounded to oval. Petal apex: Rounded. Petal margin: Entire. Petal texture, upper and lower surfaces: Smooth; satiny. Petal color: When opening, upper surface: 97A to 97B; center, 92D. When opening, lower surface: 97D; towards the base, 155D. Fully opened, upper surface: 97A; center, 155D; nectar guides at base of banner petals, 90A. Fully opened, lower surface: 97B.

*Calyx.*—Arrangement: Cup-shaped calyx with five sepals fused at the base. Sepal length: About 1 mm. Sepal width: Less than 1 mm. Sepal shape: Elliptic. Sepal apex: Acute. Sepal margin: Entire. Sepal texture, upper and lower surfaces: Minutely tomentose. Sepal color, developing, upper and lower surfaces: 148B. Sepal color, fully expanded, upper and lower surfaces: 148A.

*Peduncles.*—Length: About 20 cm. Diameter: About 3 mm. Strength: Strong. Angle: Mostly upright. Texture: Tomentose. Color: 183A.

*Pedicels.*—Length: About 6 mm. Diameter: Less than 1 mm. Strength: Strong. Angle: Nearly horizontal. Texture: Minutely tomentose. Color: 183A.

*Reproductive organs.*—Stamens: Quantity per flower: Four. Anther shape: Oval. Anther length: Less than 1 mm. Anther color: 94A. Pollen amount: Scarce. Pollen color: 158A. Pistils: Quantity per flower: One. Pistil length: About 1 cm. Style length: About 9 mm. Style color: 97D. Stigma shape: Bi-parted. Stigma color: 97A. Ovary color: 148A.

*Seed/fruit.*—Seed nor fruit production has not been observed.

Disease/pest resistance: Plants of the new *Plectranthus* have not been noted to be resistant to pathogens or pests common to *Plectranthus.*

Garden performance: Plants of the new *Plectranthus* have been observed to have good garden performance and to be tolerant to rain, wind and temperatures ranging from 5 to 38° C.

It is claimed:

1. A new and distinct cultivar of *Plectranthus* plant named 'Limplep 1', as illustrated and described.

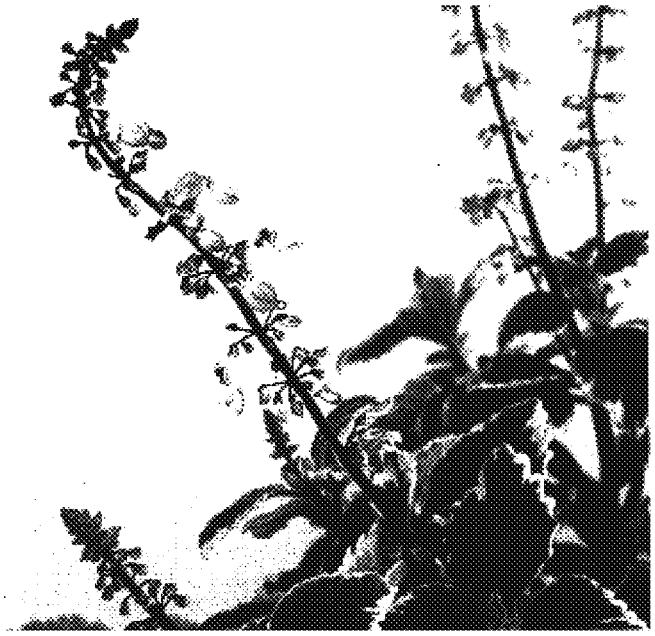
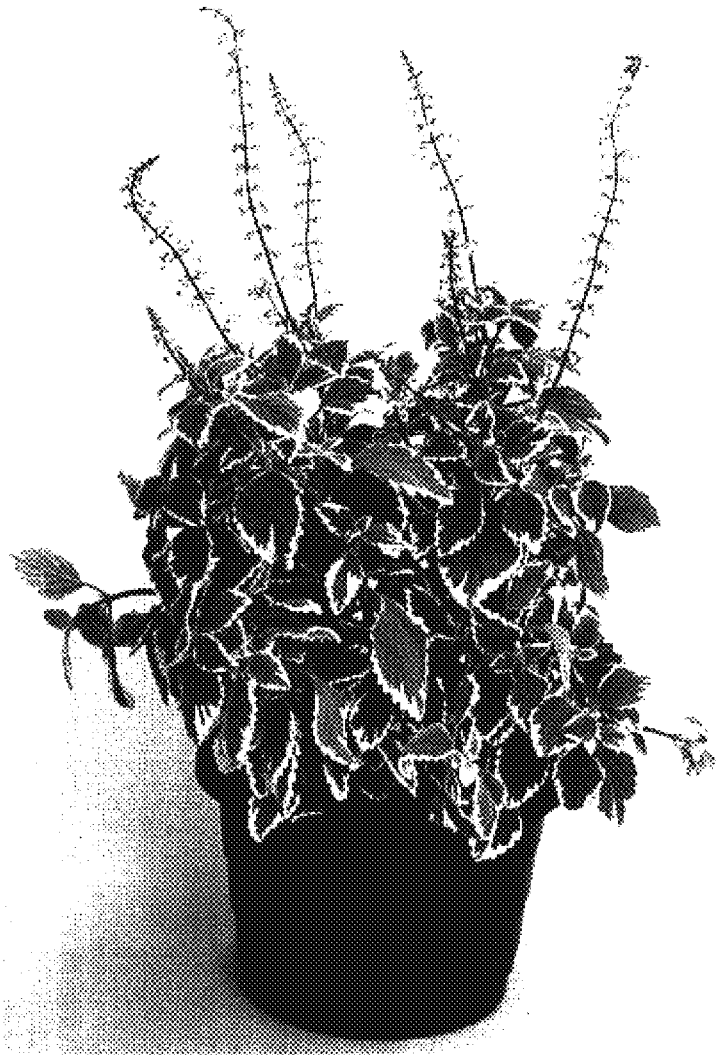

* * * * *